US00PP16722P2

(12) United States Plant Patent
Bartels

(10) Patent No.: US PP16,722 P2
(45) Date of Patent: Jun. 27, 2006

(54) ***PHLOX* PLANT NAMED 'BARTHIRTYFIVE'**

(50) Latin Name: *Phlox paniculata*
Varietal Denomination: Barthirtyfive

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 61 days.

(21) Appl. No.: 11/077,408

(22) Filed: Mar. 10, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Anne Marie Grunberg
(74) *Attorney, Agent, or Firm*—C. A. Whealy

(57) ABSTRACT

A new and distinct cultivar of *Phlox* plant named 'Barthirtyfive', characterized by its upright and compact plant habit; freely branching growth habit; light red purple and white bi-colored flowers; freely flowering habit; and good garden performance.

1 Drawing Sheet

Botanical designation: *Phlox paniculata.*
Cultivar denomination: 'Barthirtyfive'.

BACKGROUND OF THE INVENTION

The present Invention relates to a new and distinct cultivar of *Phlox* plant, botanically known as *Phlox paniculata,* and hereinafter referred to by the cultivar name Barthirtyfive.

The new *Phlox* is a product of a planned breeding program conducted by the Inventor in Aalsmeer, The Netherlands. The objective of the breeding program was to create new compact pot-type *Phlox* cultivars with numerous flowers with attractive leaf and flower coloration.

The new *Phlox* originated from a cross-pollination made by the Inventor in Aalsmeer, The Netherlands of a proprietary selection of *Phlox paniculata* identified as code number 98.4, not patented, as the female, or seed, parent with a proprietary selection of *Phlox paniculata* identified as code number 94.44.38.02, not patented, as the male, or pollen, parent. The new *Phlox* was discovered and selected by the Inventor as a flowering plant within the progeny of the stated cross-pollination in a controlled environment in Aalsmeer, The Netherlands.

Asexual reproduction of the new cultivar by terminal cuttings since 2002 in Aalsmeer, The Netherlands, has shown that the unique features of this new *Phlox* are stable and reproduced true to type in successive generations.

SUMMARY OF THE INVENTION

Plants of the cultivar Barthirtyfive have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Barthirtyfive'. These characteristics in combination distinguish 'Barthirtyfive' as a new and distinct cultivar:

1. Upright and compact plant habit.
2. Freely branching growth habit.
3. Light red purple and white bi-colored flowers.

4. Freely flowering habit.
5. Good garden performance.

Plants of the new *Phlox* differ primarily from plants of the parent selections in flower coloration.

Plants of the new *Phlox* can be compared to plants of the *Phlox paniculata* cultivar Barten, disclosed in U.S. Plant Pat. No. 11,802. In side-by-side comparisons conducted in Aalsmeer, The Netherlands, plants of the new *Phlox* differed from plants of the cultivar Barten primarily in flower color as plants of the cultivar Barten had lavender-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new *Phlox.* The photograph comprises a side perspective view of typical flowering plants of 'Barthirtyfive' grown in an outdoor nursery.

DETAILED BOTANICAL DESCRIPTION

The aforementioned photograph, following observations and measurements describe plants grown in Aalsmeer, The Netherlands, in an outdoor nursery under commercial production practices during the summer. Plants were about three months old when the photograph and description were taken. During the production of the plants, day temperatures averaged 20° C. and night temperatures averaged 15° C. In the following description, color references are made to The Royal Horticultural Society Colour Chart, 1995 Edition, except where general terms of ordinary dictionary significance are used.

Botanical classification: *Phlox paniculata* cultivar Barthirtyfive.

Parentage:

*Female parent.*—Proprietary selection of *Phlox paniculata* identified as code number 98.4, not patented.

*Male parent.*—Proprietary selection of *Phlox paniculata* identified as code number 94.44.38.02, not patented.

Propagation:

*Type cutting.*—Vegetative cuttings.

*Time to initiate roots, summer.*—About three weeks at 25° C.

*Time to initiate roots, winter.*—About four weeks at 18° C.

*Time to produce a rooted young plant, summer.*—About five weeks at 25° C.

*Time to produce a rooted young plant, winter.*—About six to seven weeks at 18° C.

*Root description.*—Thick, fleshy; white in color.

*Rooting habit.*—Freely branching; moderately dense.

Plant description:

*Plant form/habit.*—Upright and compact plant habit; narrow inverted triangle. Freely branching with about ten lateral branches per plant.

*Plant height.*—About 50 cm.

*Plant width* (*spread*).—About 30 cm.

*Lateral branches.*—Length: About 10 cm. Diameter: About 6 to 9 mm. Internode length: About 1.5 cm. Strength: Strong. Texture: Pubescent. Color: 144A.

*Foliage description.*—Arrangement: Alternate, simple; sessile. Length: About 8 cm. Width: About 4 cm. Shape: Oblong to elliptic. Apex: Acuminate. Base: Obtuse. Margin: Entire. Texture, upper and lower surfaces: Smooth, glabrous; leathery. Venation pattern: Pinnate. Color: Developing and fully developed leaves, upper surface: 137A. Developing and fully developed leaves, lower surface: 137C. Venation, upper and lower surfaces: 144B.

Flower description:

*Flower type/habit.*—Single, rounded salverform flowers arranged in terminal panicles; panicles globular to pyramidal in form; flowers face upright and outward. Freely flowering habit with about 50 to 90 flower buds and open flowers per panicle.

*Fragrance.*—Typical of species.

*Natural flowering season.*—Continuously flowering from spring through fall in The Netherlands. Flowers not persistent.

*Postproduction longevity.*—Flowers last about four days on the plant.

*Flower buds.*—Height: About 2 cm. Diameter: About 5 mm. Shape: Elliptic. Color: 66C.

*Inflorescence height.*—About 10 cm.

*Inflorescence diameter.*—About 10 cm.

*Flower diameter.*—About 3 cm.

*Flower length.*—About 1 cm.

*Petals.*—Quantity per flower: Typically five in a single whorl; petals fused at the base into a narrow tube. Length (including tube): About 2.5 cm. Width: About 1 cm. Shape: Obovate. Apex: Rounded. Margin: Entire. Aspect: Mostly flat. Texture, upper and lower surfaces: Smooth, glabrous. Color: Developing petals, upper surface: 66C. Developing petals, lower surface: 66D. Fully expanded petals, upper surface: 66C to 66D; towards the base, 155C. Fully expanded petals, lower surface: 66D. Throat: 155C. Tube: 60A.

*Sepals.*—Quantity per flower: Typically five in a single whorl, fused; narrow tubular calyx. Length: About 5 mm. Width: About 3 mm. Shape: Lanceolate. Apex: Acuminate. Texture, upper and lower surfaces: Smooth, glabrous. Color, upper and lower surfaces: 137A.

*Pedicels.*—Length: About 1 cm. Diameter: About 2 mm. Orientation: Upright to about 45° from vertical. Strength: Strong. Color: 145A.

*Reproductive organs.*—Stamens: Quantity per flower: Typically five. Anther shape: Oblong. Anther length: About 2 mm. Anther color: 155A. Pollen amount: Scarce. Pollen color: Close to 155D. Pistils: Quantity per flower: Typically one. Pistil length: About 2.5 cm. Stigma shape: Tri-parted. Stigma color: 154D. Style length: About 2.5 cm. Style color: 154D. Ovary color: 137D.

Disease/pest resistance: Plants of the new *Phlox* have been noted to be resistant to Powdery Mildew. Plants of the new *Phlox* have not been noted to be resistant to other pathogens and pests common to *Phlox*.

Garden performance: Plants of the new *Phlox* have been observed to have good garden performance and tolerate rain, wind and temperatures ranging from 0 to about 35° C.

It is claimed:

1. A new and distinct cultivar of *Phlox* plant named 'Barthirtyfive', as illustrated and described.

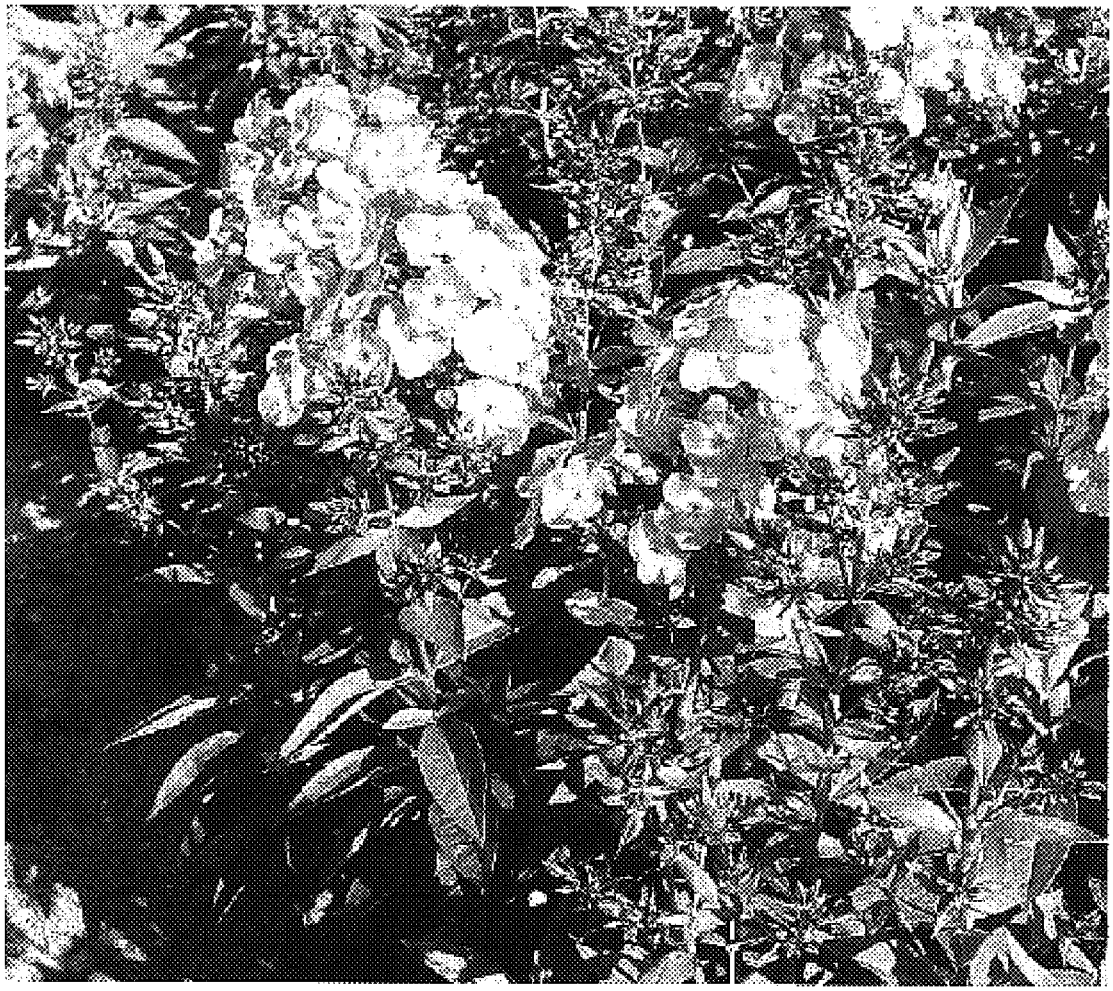

* * * * *